(12) United States Patent
Bayon et al.

(10) Patent No.: US 7,904,987 B2
(45) Date of Patent: Mar. 15, 2011

(54) CLEANING TOOL

(75) Inventors: F. Antonio Bayon, Newtown, PA (US); Jess W. Roche, Ardmore, PA (US); Albert Esing, Jr., Phoenixville, PA (US); Vince Juniana, Exton, PA (US)

(73) Assignee: MagnaWand, Inc., Newtown, PA (US)

( * ) Notice: Subject to any disclaimer, the term of this patent is extended or adjusted under 35 U.S.C. 154(b) by 944 days.

(21) Appl. No.: 11/697,261

(22) Filed: Apr. 5, 2007

(65) Prior Publication Data
US 2008/0244846 A1 Oct. 9, 2008

(51) Int. Cl.
*A47L 13/17* (2006.01)
(52) U.S. Cl. .................. 15/104.94; 15/210.1; 15/244.1
(58) Field of Classification Search ............... 15/104.94, 15/210.1, 244.1
See application file for complete search history.

(56) References Cited

U.S. PATENT DOCUMENTS

| | | | |
|---|---|---|---|
| 3,383,158 A * | 5/1968 | Leland | 401/201 |
| 4,415,288 A | 11/1983 | Gordon et al. | |
| 4,507,111 A | 3/1985 | Gordon et al. | |
| 4,592,347 A | 6/1986 | Mahruki | |
| 4,856,136 A | 8/1989 | Janssen | |
| 5,336,219 A | 8/1994 | Krantz | |
| 5,383,900 A | 1/1995 | Krantz | |
| 5,445,462 A | 8/1995 | Johnson et al. | |
| 5,528,791 A | 6/1996 | Wilson | |
| 5,538,353 A | 7/1996 | DeHavilland | |
| 5,603,138 A | 2/1997 | Bonis | |
| 5,690,958 A | 11/1997 | McGrath | |
| 5,772,346 A | 6/1998 | Edwards | |
| D396,911 S | 8/1998 | DeHavilland | |
| 5,875,511 A | 3/1999 | Nejdl | |
| 5,918,342 A | 7/1999 | Smith et al. | |
| 5,960,508 A | 10/1999 | Holt et al. | |
| 6,093,255 A | 7/2000 | Smith et al. | |
| 6,349,443 B1 | 2/2002 | Randolph et al. | |
| 6,546,584 B2 | 4/2003 | Hobden | |
| 6,991,393 B2 | 1/2006 | Tufts et al. | |
| 6,991,394 B2 | 1/2006 | Tufts et al. | |
| 7,032,270 B2 | 4/2006 | Vitantonio et al. | |
| 7,386,910 B2 * | 6/2008 | Minkler et al. | 15/145 |
| 2006/0225237 A1 * | 10/2006 | Gartland | 15/210.1 |

OTHER PUBLICATIONS

Internet Catalog at www.puritanmedproducts.com—Puritan Products, downloaded Apr. 4, 2006.
Internet Catalog at www.medi-flex.com—Mediflex, Inc., downloaded Apr. 4, 2006.

* cited by examiner

*Primary Examiner* — Randall Chin
(74) *Attorney, Agent, or Firm* — Joseph M. Konieczny, Sr.; Ryder, Lu, Mazzeo & Konieczny

(57) ABSTRACT

A cleaning device including an elongate wand, a cleaning cartridge with an attachment portion, and means for releasably attaching and detaching the cleaning cartridge to the opposite end of the wand. The attachment and detachment means has an ejector collar slidably fixed to the second end of the wand and movable between extended and retracted positions. The collar includes a pair of collar jaws. The attachment and detachment means also has a pair of clamp jaws on the second end of the wand lying within the ejector collar. The clamp jaws are in near abutment with an inside surface of the collar when the collar is in the retracted position. The cartridge is attached to the wand by inserting the attachment portion between the clamp jaws and clamping the clamp jaws on the attachment portion. The cartridge is detached from the wand by pushing the ejector collar along the wand body away from the second end of the wand and against the cartridge.

20 Claims, 11 Drawing Sheets

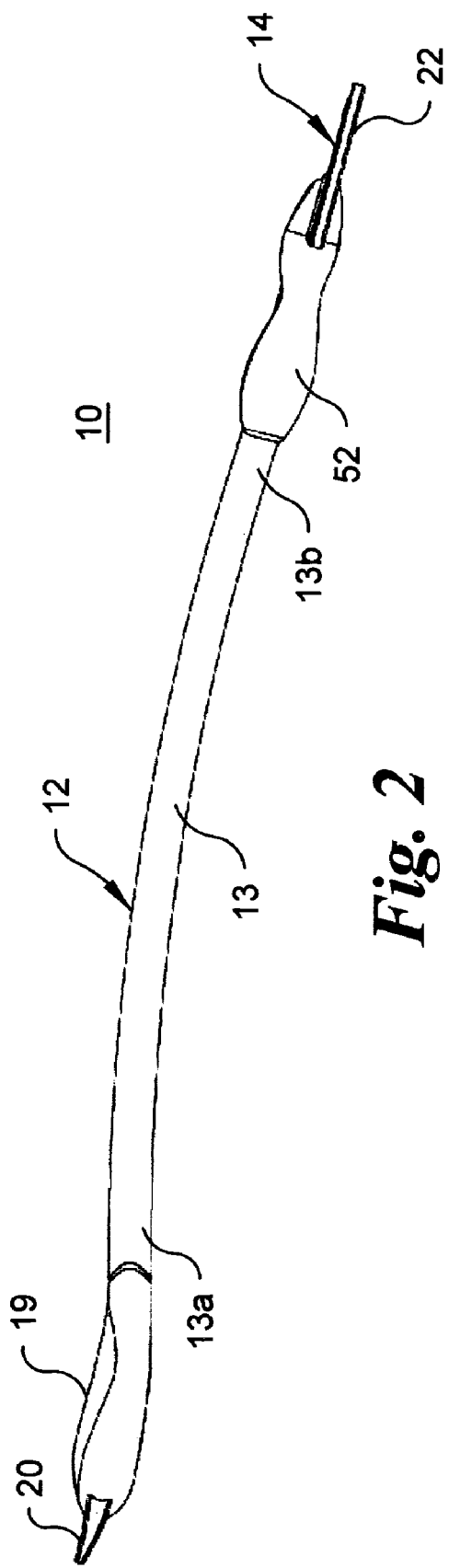

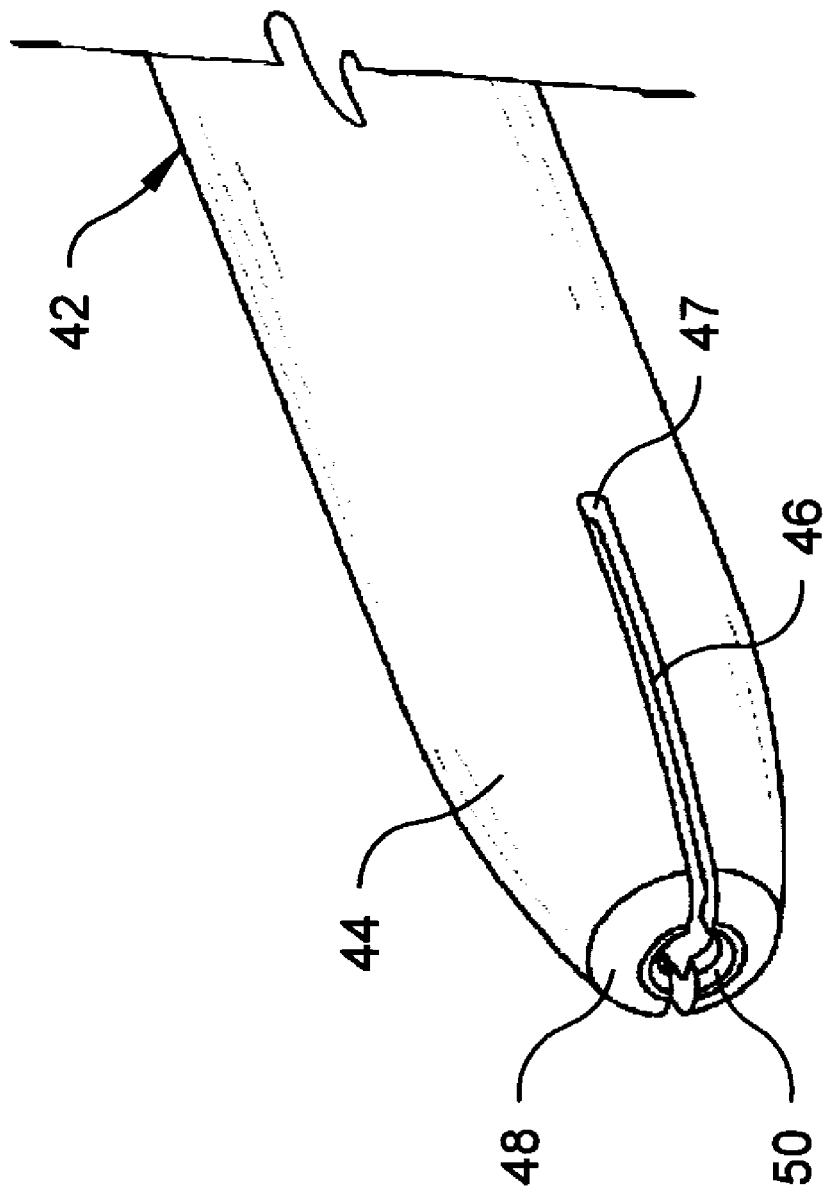

CLEANING TOOL

FIELD OF THE INVENTION

The present invention relates to a tool for cleaning difficult to reach, biologically-contaminated surfaces such as the interior, patient-occupied, scanning areas of medical devices such as MRI, CAT, and PET scanners.

BACKGROUND OF THE INVENTION

MRI, CAT and PET scanners, especially inside the magnet bore, PET tunnel, or CT gantry, are very rarely cleaned because they are very hard to access. In order to clean thoroughly the internal, patient-occupied, scanning areas, one must crawl inside the bore or "tunnel" and clean within a very tight, confined area. Even if the inside of a scanner was more easily accessible, technicians have little time between patient visits (about 5-10 minutes on average) to crawl inside and thoroughly clean these tight spaces. Some of the cleaning products currently on the market, i.e., wipes or disinfectants, simply do not reach the above-described internal, patient-occupied, scanning areas and can be very expensive. As a result, patient scanners are a contamination source and contribute to the spread of resistant bacteria in hospitals.

As a general matter, there is a great public interest in creating cleaner and safer medical environments and, in particular, cleaner medical equipment that routinely contacts patients. To achieve this goal, it is desirable to provide a tool that will reach the internal, patient-occupied, scanning areas of scanners and any other areas where the risk of bacteria contamination may exist. To eliminate cross-contamination, it is also desirable to provide a tool that has a disposable cleaning surface and can be used with a disinfectant or sanitizer that will kill bacteria on contact.

In certain environments such as refineries and mining operations, a requirement exists that any tool used therein be non-sparking. In certain other magnetically-sensitive areas, a requirement exists that any tool used therein be non-magnetic. Thus, it would also be desirable to provide a non-sparking and non-magnetic cleaning tool for that can be used in such environments.

SUMMARY OF THE INVENTION

In order to meet the needs in the art explained above, the invention provides a cleaning tool that is long enough to reach inside the bore of an MRI machine from the front of the magnet to the back end. If the back end of the magnet still cannot be reached from the front, the technician may go around to the back end and clean the magnet from back to front. The magnet can be cleaned by circular action, straight action, or semi-circular action. While the cleaning tool is equipped with a long reach wand, a smaller version of the tool handle may also be used to clean the coils in which patients either lay down on or are enclosed. Coils such as a "head coil," "knee coil," "cervical coil," and "thoracic coil" are examples of the coils that can be cleaned with a shorter handled version of the tool of the present invention. The shorter handle uses the same or differing disposable cleaning implements as the longer handle. Either version of the invention can also be used to clean X-ray machines, nuclear medicine, ultrasound equipment, or any other hospital radiological equipment.

One highly-preferred feature of all hospital cleaning equipment is disposability. To this end, the cleaning tool of the present invention includes a disposable cleaning cartridge, which is releasably attached to the end of the tool by a snap-fit action. The disposable cartridge is ejected by a mechanism that does not require the technician to contact the contaminated cartridge. The cartridges may be provided in different densities, textures and sizes to achieve the desired cleaning effect. For example, a sponge cartridge can be used to provide general cleaning and disinfecting. A cartridge with a scrub texture can be used to scrub and clean difficult stains. A paper wipe cartridge can be used to sanitize and disinfect areas that are easier to clean. In all cases, the cleaning tool of the invention is preferably used with a liquid cleaner or sanitizer that is EPA and USDA approved.

More specifically, the invention comprises a cleaning device consisting of an elongate wand having a central body with a handle at a first end and a cleaning cartridge releasably attached at the opposite second end between resilient clamp jaws. The mechanism for releasably attaching and detaching the cleaning cartridge includes an ejector collar, which is affixed to the second end of the wand is movable between extended (ejection) and retracted (operative) positions. The collar includes a pair of opposed, collar jaws, which engage the engagement portion of the back plate of the cartridge. The cartridge is ejected from between the clamp jaws by pushing the ejector collar along the wand body. The ejector collar includes a nose portion, which pushes against a closely fitting pocket in the attachment portion of the back plate as the collar is moved to the extended or ejection position. The attachment portion of the back plate includes a retaining nub upwardly extending from its planar surface. The nub is captured behind the clamp jaws to lock the cartridge into snap, friction-fit engagement. When the ejector collar is in its retracted position, the clamp jaws and collar jaws are dimensioned to provide an interference or snap-fit engagement with the wiper plate in the space between the pocket and the retaining nub. The back plate pocket includes a semi-circular rim along its periphery, which abuts a corresponding surface on the nose portion of the ejector collar to provide torsional resistance between the wand and the cartridge. The back plate is preferably composed of resilient plastic and further includes a laterally-extending living hinge, which allows the cleaning implement to deflect angularly.

While the cleaning tool may be used in any environment, in a preferred embodiment the cleaning tool is used to clean MRI scanners. In this embodiment, the cleaning tool is made from non-ferrous materials. The tool is also non-sparking, which qualifies its use in explosive environments. The device is cost effective, easy to use, and prevents cross contamination because the cleaning cartridges are easy to dispose.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

FIG. 2 is a side elevation of the cleaning tool of FIG. 1;

FIG. 5 is an enlarged, fragmentary, perspective of one end of the wand body of the cleaning tool of FIG. 1;

DESCRIPTION OF THE PREFERRED EMBODIMENT

For the purpose of illustrating the invention, there is shown in the accompanying drawings embodiments of the invention. However, it should be understood by those of ordinary skill in the art that the invention is not limited to the precise arrangements and instrumentalities shown therein and described below.

Figure 1:
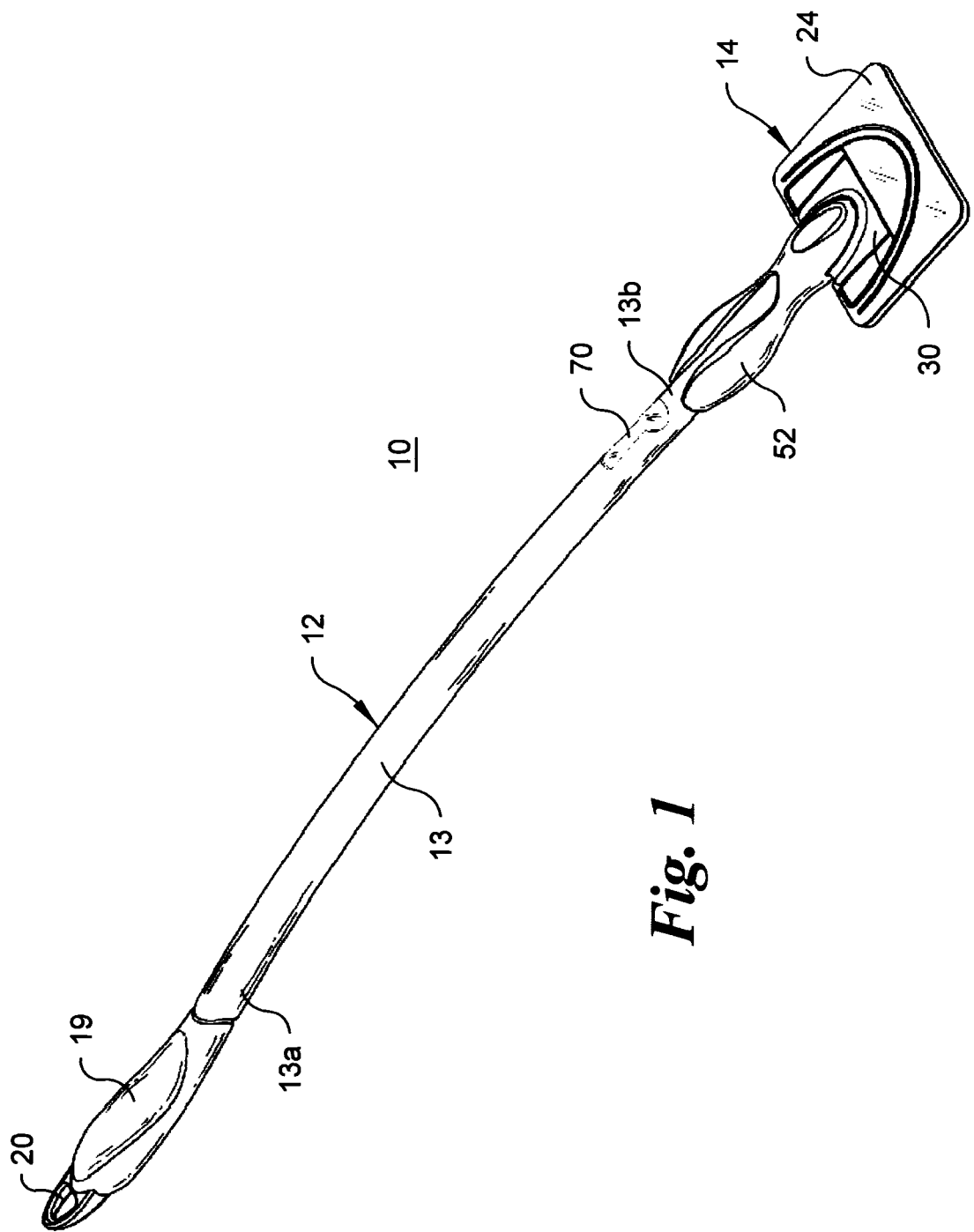
FIG. 1 is a perspective view of a cleaning tool in accordance with an embodiment of the invention.

The cleaning device in accordance with a first embodiment of the present invention is illustrated in FIGS. 1-9 wherein like reference numerals are used throughout to designate like elements. Referring now to FIG. 1, the cleaning device, designated generally by reference numeral 10, comprises a wand 12, a disposable cleaning cartridge 14, and a mechanism 16 for releasably attaching and detaching the cleaning cartridge 14 to and from, respectively, the wand 12. Preferably, the mechanism 16 allows the cartridge 14 to pivot relative the wand 12. The mechanism 16 detaches the cartridge 14 from the wand 12 without requiring the user to handle or contact the cleaning cartridge 14.

The wand 12 has an elongate body portion 13 with first 13a and second 13b ends. In a preferred embodiment, the body portion 13 comprises a lightweight, hollow tube made from a non-metallic material such as plastic. The length of the body portion 13 may vary but should be long enough so that a maintenance technician can easily reach into the internal, patient-occupied areas of an MRI, CAT or PET scanner, especially inside the magnet bore, PET tunnel, or CT gantry. In a preferred embodiment, the length of the wand is about 34 inches. The diameter and thickness of the tube wall will vary with tube length and should be selected to provide adequate rigidity without excess weight. For example, for a wand length of about 34 inches, the tube may have a 0.875 inch diameter and a wall thickness of about 0.10 inches and be made from high density polyethylene ("HDPE").

In a preferred embodiment, the wand 12 has a slight arc as best seen in FIG. 2. The arc provides a greater range of motion for cleaning the scanner. The wand may also include a recessed pocket 70, wherein identifying indicia, such as a label, may be applied.

A handle 19 is formed on or attached to the first end 13a of the wand 12. As best seen in FIGS. 1 and 2, the handle 19 has a contour that compliments the grip of a human hand. Preferably, the handle 19 is made from a material that is easy to grip and is sanitizable. For example, the handle may be made from HDPE. Preferably, the handle 19 includes an integrally-formed eyelet 20, which allows the device 10 to be hung from a hook for storage, or to be secured to the scanner via a chain or cable.

In a preferred embodiment, the cartridge 14 is disposable and comprises a cleaning pad 22 fixed to a supporting back plate 24. The cleaning pad 22 may be adhered or fixed with fasteners to the back plate 24. In the embodiment shown in FIGS. 1-9, the cartridge is generally planar and rectangular, and is approximately 4 inches long (measured in the direction of the lengthwise axis of the wand 12) by 5 inches wide; however, the shape and size of the cartridge 14 may be modified for particular cleaning applications without departing from the scope of the invention. The properties, such as grit and absorbency, of the cleaning pad 22 may also vary depending on the intended application. For example, the cleaning pad 22 may comprise a layer of sponge, felt, scouring, or squeegee material. In a preferred embodiment, the cleaning pad 22 is absorbent so that a maintenance technician can impregnate the cleaning pad with a cleaning solution prior to use. Alternatively, the cartridge 14 can be prepackaged in a sealed, liquid-tight container with a cleaning solution impregnated in the cleaning pad 22.

The back plate 24 is made from a thin, rigid material. In single-use applications, the back plate 24 may be made of cardboard; however, the back plate 24 may be made of a more durable material such as plastic if the cartridge 14 is intended to be used more than once. For increased rigidity, the back plate 24 may have one or more stiffening ribs 26, 28, which also serve to decorate the cartridge.

The cartridge 14 is releasably attached to the second end of the wand 12. In the embodiment illustrated in FIGS. 1-9, the attachment mechanism includes a leaf 30 that is hinged to the back plate 24 and a clamp 42 that is connected to the second end of the wand 12. While the leaf 30 of this embodiment has a single degree of freedom, other forms of leaf 30 having two or three degrees of freedom could also be utilized.

Figure 4:
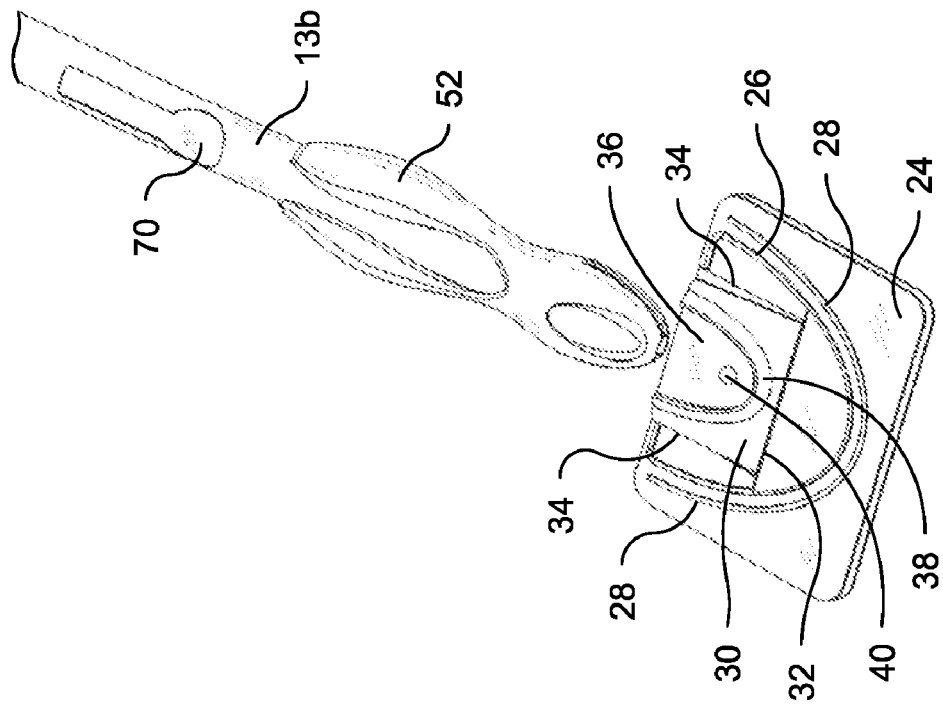
FIG. 4 is an enlarged, fragmentary, perspective of the cleaning cartridge detached from the wand of the cleaning tool of FIG. 1.
Figure 3:
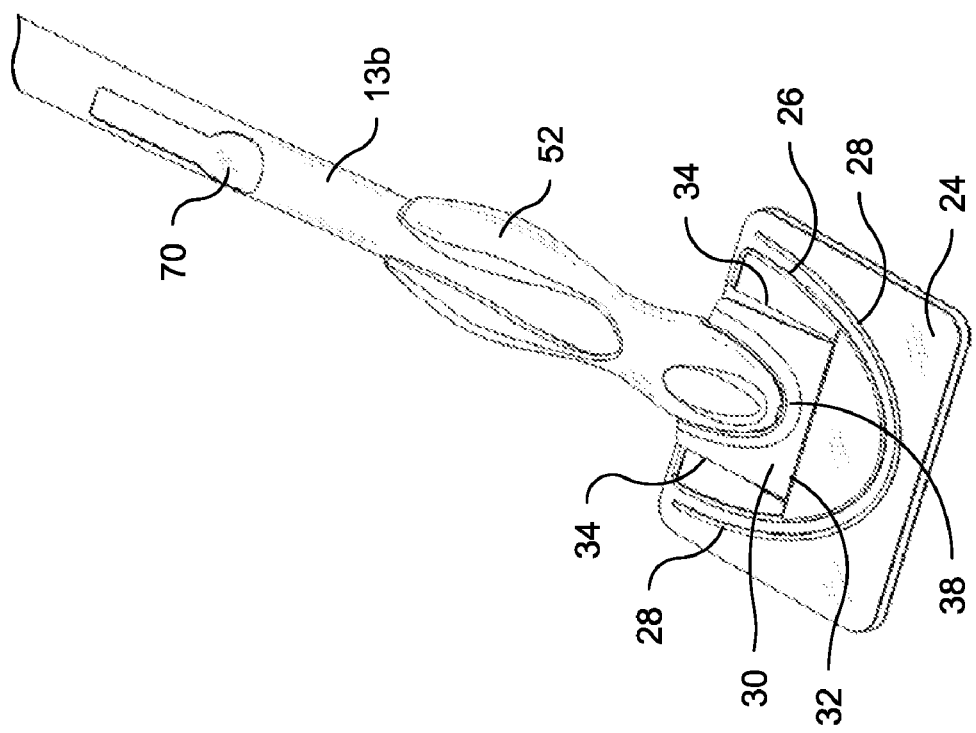
FIG. 3 is an enlarged, fragmentary, perspective of the cleaning cartridge attached to the wand of the cleaning tool of FIG. 1.
Figure 6:
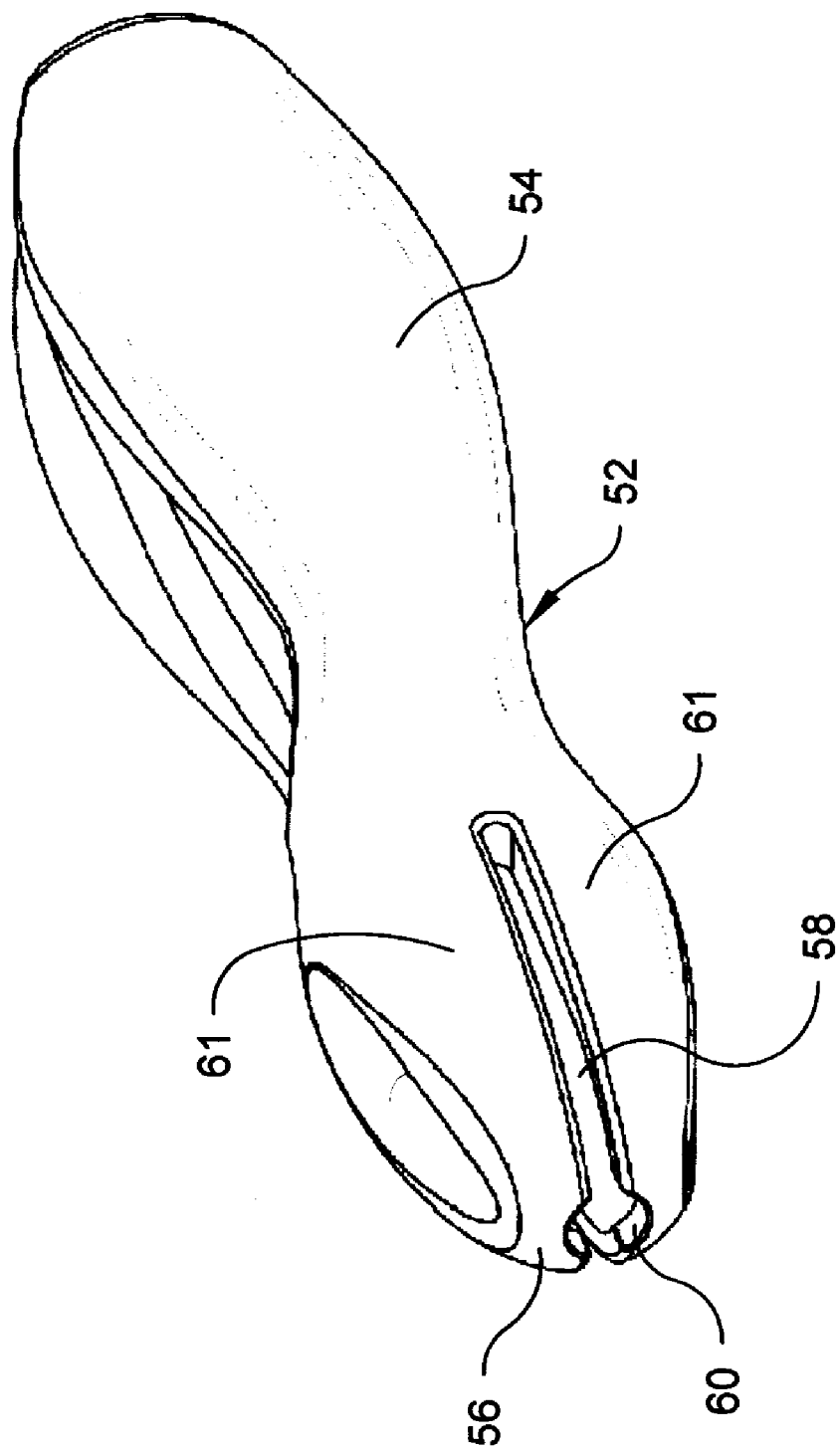
FIG. 6 is an enlarged, fragmentary, perspective of the ejection collar of the cleaning tool of FIG. 1.

Referring to FIGS. 3 and 4, the leaf 30 comprises a tab portion of the back plate 24 that is partially cut from the back plate 24 along two cut lines 34 and partially connected to and rotatable relative to the back plate 24 along a linear hinge interface 32. In contrast with the remaining portion of the back plate 24, the tab portion is not adhered or fixed to the cleaning pad 22 so that the tap portion can rotate relative thereto. The linear hinge interface 32 is formed by scoring or pressing a hinge line extending between the terminus of each cut 34.

As best seen in FIG. 4, a raised, horseshoe-shaped rim 38 on the outer surface of the leaf 30 defines a pocket 36 into which the ejection collar 52, described below, nests when the cartridge 14 is connected to the wand 12. Preferably, the contour of the pocket 36 and the nose 56 of the ejection collar 52 compliment one another to ensure a firm interface between them. A detent is formed in the pocket 36 on the outer surface of the leaf 30. In a preferred embodiment, the detent comprises a hemispherical nub 40. As described in greater detail below, the nub 40 engages the clamp jaws 44 to lock the cartridge 14 on the wand 12.

Referring to FIG. 5, the clamp 42 comprises a pair of jaws 44 at the second end of the wand 12. The jaws 44 are formed by cutting an axial slot 46 in the end of the wand 12. The axial slot 46 has a thickness slightly smaller than the thickness of the leaf 30 and a depth approximately equal to the depth of the pocket 36 in the leaf 30. The inner end 47 of the slot is rounded to prevent the slot 46 from cracking. The jaws 44 taper to a nose 48 having a reduced-diameter end surface. A chamfered bore 50 extends through the nose 48 to the internal cavity of the wand 12. The radius of the bore 50 is smaller than the radius of the nub 40. The nub 40 can pass through the bore 50 and the leaf 30 can slide into the slot because the jaws 44 deflect slightly to provide a snug friction interference/connection between the leaf 30 and the jaws 44.

Figure 7:
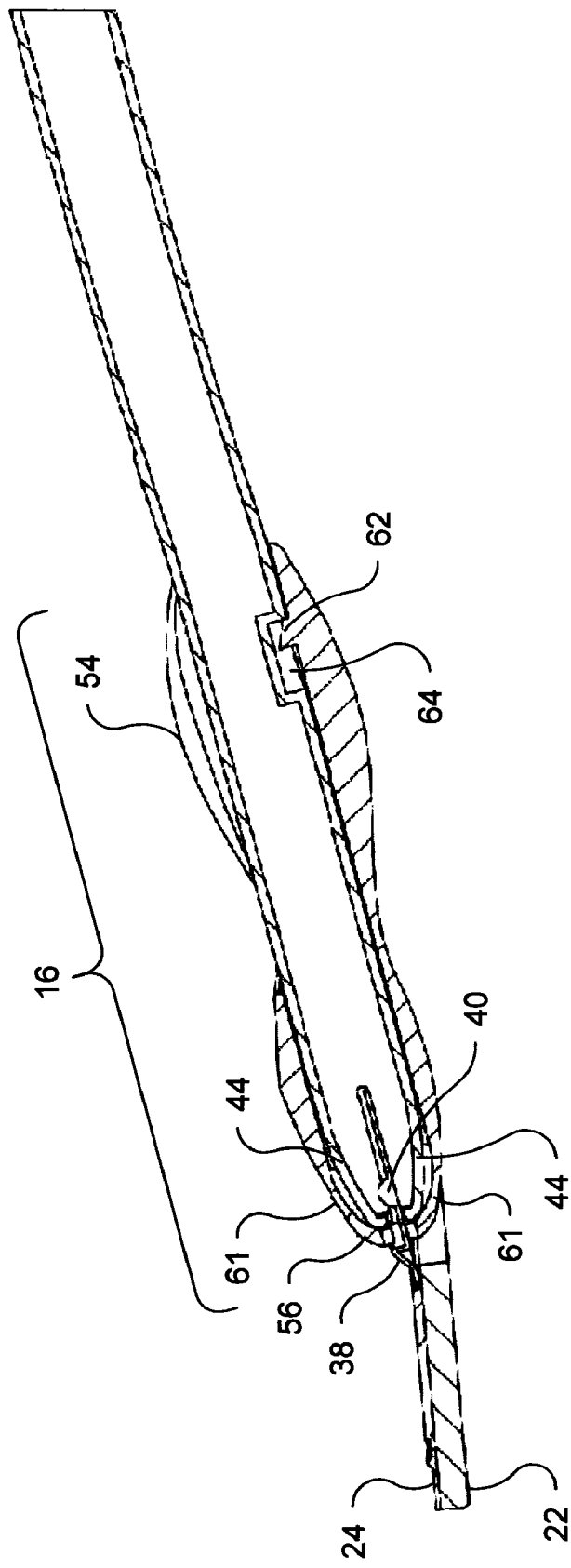
FIGS. 7-9 are side, sectional views showing sequential steps of engagement and disengagement of the cartridge with the wand.
Figure 8:
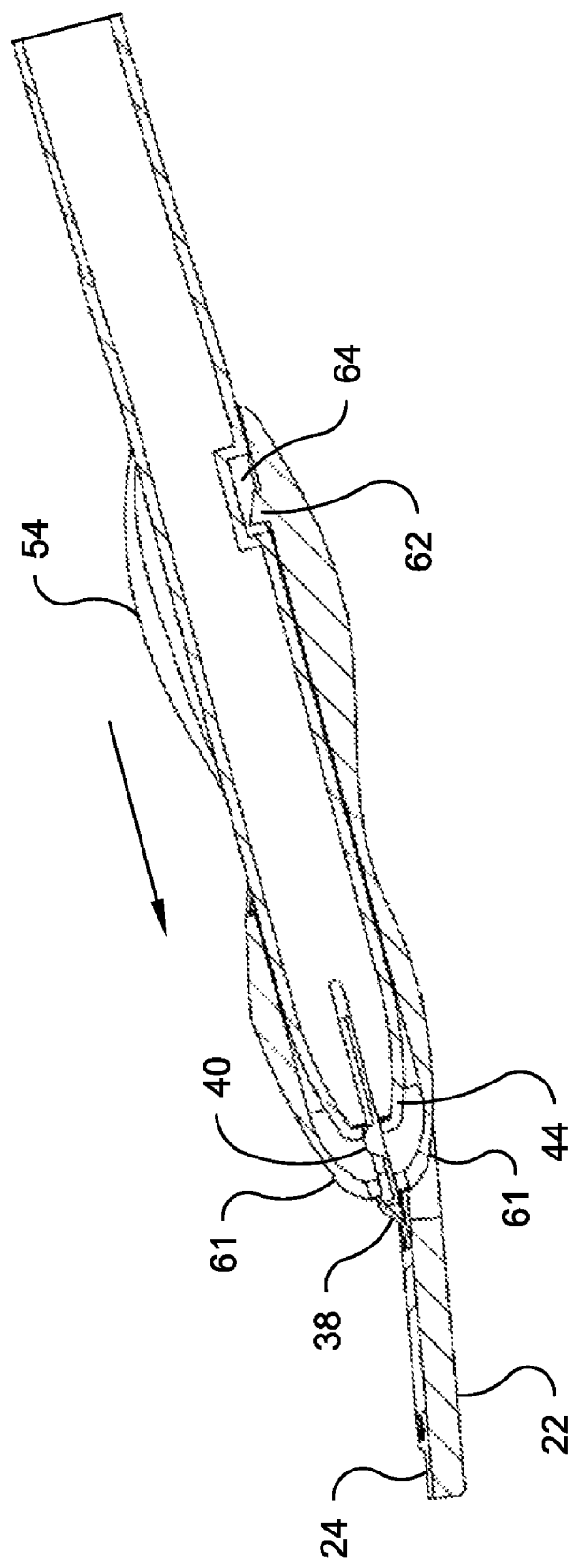
Figure 9:
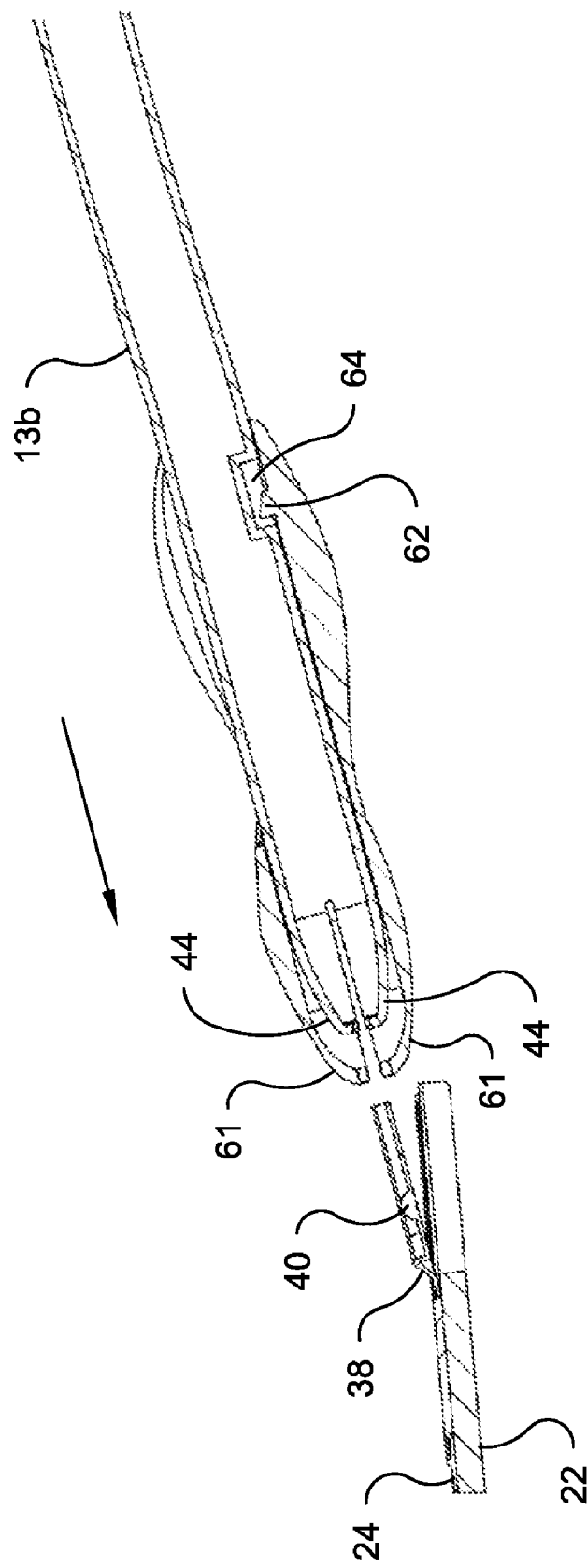

An ejection collar 52 surrounds and is slidably fixed to the clamp 42. As best seen in FIGS. 7-9, the collar 52 is movable between extended and retracted positions. In the retracted position shown in FIG. 7, the collar 52 permits connection between the cartridge 14 and the wand 12. In the extended position shown in FIGS. 8 and 9, the collar 52 disengages and ejects the cartridge 14 from the wand 12.

Referring to FIGS. 3 and 4, the ejection collar 52 has an inner diameter slightly larger than the outer diameter of the wand 12. The outer surface 54 of the collar 52 may have a contour that compliments a human hand. Similar to the clamp 42, one end of the collar 52 tapers to a nose 56 having a reduced-diameter end surface. The contour of the nose 56 compliments the shape of the pocket 36 in the leaf 30 so that the nose 56 nests closely in the pocket 36 and resists lateral movement of the cartridge 14.

A slot 58 extends axially from the nose 56 to an intermediate point along the collar 52, thereby defining opposed jaws 61. The slot 58 has a thickness slightly larger than the thickness of the leaf 30 and a depth approximately equal to the depth of the pocket 36 in the leaf 30. The slot 58 of the collar 52 is arranged to align with the slot 46 of the clamp 42 so that the leaf 30 of the cartridge 14 is captured in both slots.

Similar to the clamp 42, a chamfered bore 60 extends through the nose 56 of the collar 52; however, in contrast with the clamp 42, the radius of the bore 60 is larger than the radius of the nub so that the nub 40 can freely pass therethrough when the cartridge 14 is ejected.

Referring to FIGS. 7-9, a stop nub 62 is fixed to the inner surface of the collar 52 and extends radially-inwardly into a limit slot 64 in the wand 12. The stop nub 62 and limit slot 64 define the range of travel of the collar 52 along the wand 12.

Engagement and disengagement of the cartridge 14 with the wand 12 are sequentially shown in FIGS. 7-9. In FIG. 7, the cartridge 14 is shown fully connected with the wand 12. The cartridge is connected by forcibly inserting the leaf 30 into the aligned slots 46, 58 of the clamp 42 and ejector collar 52, respectively. When the cartridge 14 and wand 12 are connected, the leaf 30 is clamped by the interference fit with the jaws 44 of the clamp 42. The nose 56 of the ejector collar 52 abuts the pocket rim 36 to prevent lateral movement of the cartridge 14. The nub 40 passes through to the internal side of the chamfered bore 50 to prevent axial movement of the cartridge 14. These combined structural arrangements securely but releasably attach the cartridge to the wand.

Once the cleaning tool has been used and cartridge 14 is dirty or contaminated, it can be disconnected from the wand 12 by grasping the ejection collar 52 and pushing it forward (shown by the directional arrow) to its ejection position as shown in FIGS. 8 and 9. As the collar 52 moves forward, the nub 40 advances through the chamfered bore 50 and the leaf 30 is advanced out of the clamp slot 46 as shown in FIG. 8. Because both the collar 52 and the clamp 42 are convergent in the direction of the their respective nose portions, a substantial gap is created between the outside surface of the clamp jaws 44 and inside surface of the ejection collar 52, which allows the clamp jaws 44 to open by radial expansion. As the apex of the nub 40 clears the bore 50, the compressive force of the clamp jaws 44 on the rounded back side of the nub 40 propels the cartridge forward to assist in ejecting the leaf 30 from the slot 58. Once the nub 40 clears the bore 50, the cartridge 14 freely falls from the wand 12 as seen in FIG. 9 without contacting or handling the contaminated cartridge 14. The selection of materials and dimensions of the above-described components should be balanced to securely connection the cartridge and wand without requiring excess force to engage or disengage the cartridge.

The cleaning tool can be manipulated in any degree of rotation necessary to apply the cleaning pad 22 directly against internal surfaces of the scanner. The hinge of the cartridge 14 permits the cleaning pad 22 to follow the contour of the surface. To help trap dirt particles and disinfect the surface, the cleaning pad 22 may be impregnated with a cleaning solution or disinfectant, which may be applied either before or after the cartridge is connected to the wand. The cartridge 14 may also be prepackaged in a sealed, liquid-tight container with the cleaning solution or disinfectant impregnated in the cleaning pad.

In another embodiment of the invention, a plurality of individual, pre-packaged, disposable cartridges are provided in a container. The cartridges have a cleaning solution impregnated in the cleaning pad. The container may contain a variety of cartridges having different cleaning solutions or different surface textures.

Figure 10:
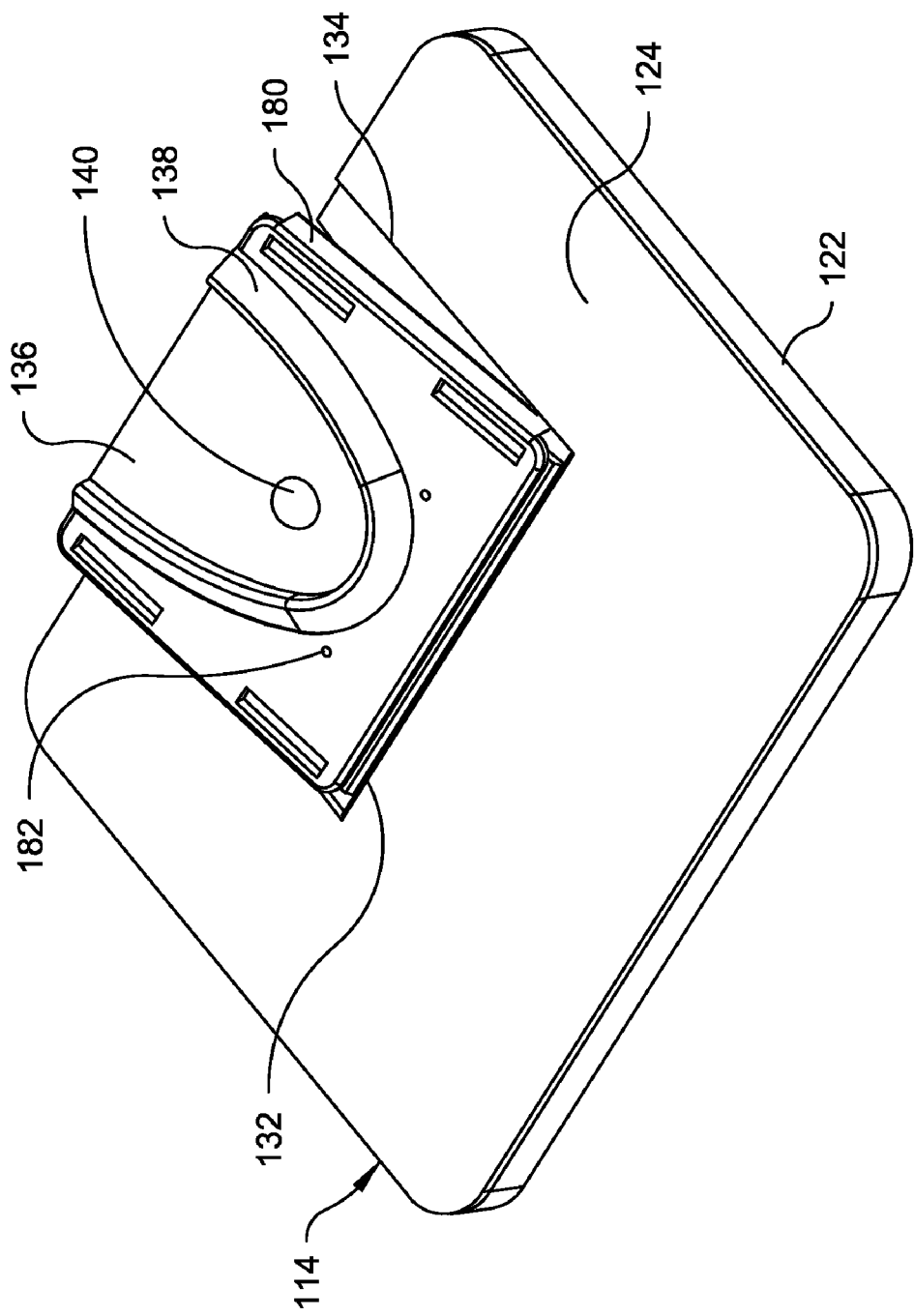
FIG. 10 is a perspective of a cleaning cartridge in accordance with another embodiment of the invention.
Figure 11:
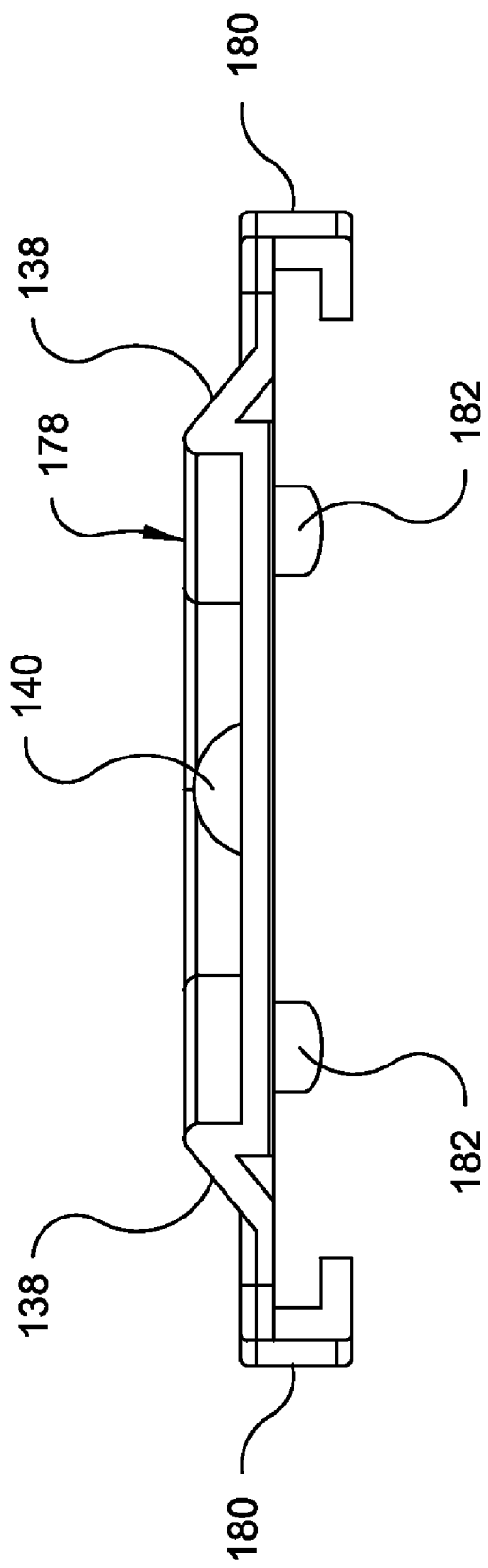
FIG. 11 is a back elevational view of an attachment clip of the cleaning cartridge shown in FIG. 10; and, FIG. 12 is a top plan view of the cardboard support back plate of the cartridge shown in FIG. 10.
Figure 12:
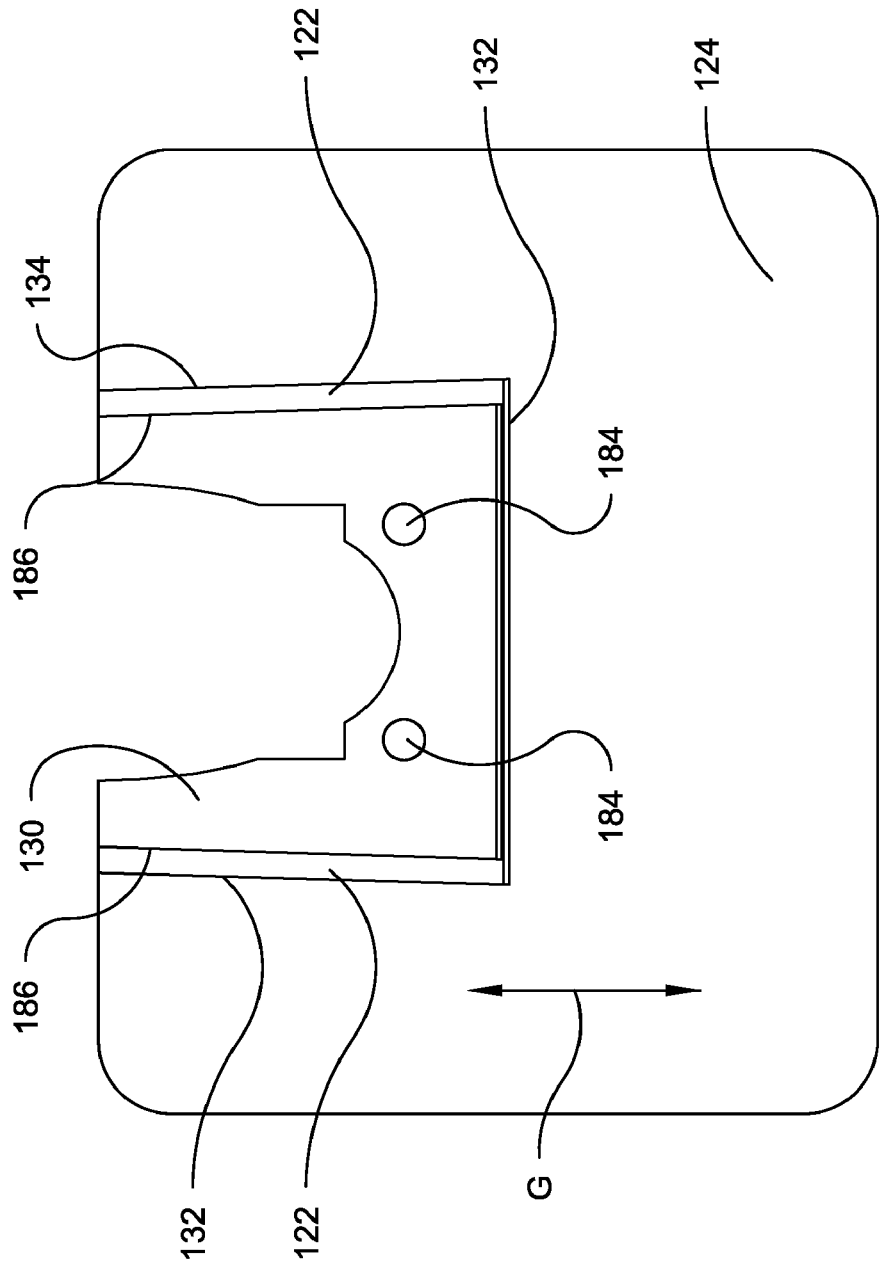

The cleaning cartridge 114 of a cleaning tool in accordance with another embodiment of the invention is shown in FIGS. 10-12 and is designated generally by reference numeral 114. The cleaning cartridge 114 is designed to engage and disengage with the wand 12 shown in FIGS. 1-9 in the same manner as the previously described cartridge 14. However, the cleaning cartridge 114 of this embodiment has a cheaper but less durable construction.

Referring to FIG. 10, the cartridge 114 is disposable and comprises a cleaning pad 122 fixed to a supporting back plate 124. The cleaning pad 122 is preferably adhered but may be fixed with fasteners to the back plate 124. In the embodiment shown in FIGS. 10-12, the cartridge 114 is generally planar and rectangular, and is approximately 4 inches long by 5 inches wide; however, the shape and size of the cartridge 114 may be modified for particular cleaning applications without departing from the scope of the invention. Like the cleaning pad of the cartridge 14 described above, the properties, such as grit and absorbency, of the cleaning pad 122 may also vary depending on the intended application. Preferably, the cleaning pad 122 is absorbent so that a maintenance technician can impregnate the cleaning pad 122 with a cleaning solution prior to use.

Referring to FIG. 12, in this embodiment, the back plate 124 is made from cardboard. Similar to the cartridge 14 described above, a leaf 130 is hinged to the back plate 124. As best seen in FIG. 12, the leaf 130 comprises a tab portion that is partially cut from the back plate 124 along two cut lines 134 and partially connected to and rotatable relative to the back plate 124 along a linear hinge interface 132. The tab portion is not adhered or fixed to the cleaning pad 122 so that the tab portion can rotate relative thereto. In the embodiment shown in FIGS. 10-12, a horseshoe-portion of the cleaning pad 122 is cut out intermediate the leaf 130. The linear hinge interface 132 may be formed by scoring or pressing a hinge line extending between the terminus of each cut 134 or simply bending along that line.

A reinforcement plate 178 is fastened to the leaf 130. As best seen in FIG. 11, the reinforcement plate 178 has a pair of opposed clips 180 formed along the lengthwise extending edges of the plate 178. The clips 180 engage the lengthwise extending edges 186 of the leaf 130. As best seen in FIG. 10, the reinforcement plate 178 includes a raised, horseshoe-shaped rim 138 on the outer surface of the leaf 130, which defines a pocket 136 into which the ejection collar 52, described above, nests when the cartridge 114 is connected to the wand 12. Preferably, the contour of the pocket 136 and the nose 56 of the ejection collar 52 compliment one another to ensure a firm interface between them. A detent is formed in the pocket 136 on the outer surface of the leaf 130. In a preferred embodiment, the detent comprises a hemispherical nub 140. As described in detail above, the nub 140 engages the clamp jaws 44 to lock the cartridge 114 on the wand 12.

A pair of studs 182 is fixed to and extends outwardly from the underside of the reinforcement plate 178. The studs 182 engage apertures 184 in the leaf 130. The studs 182 may be angled slightly rearwardly (toward the wand) in a barb-like manner so that the reinforcement plate 178 easily slides onto the leaf 130 during assembly, but will not allow the reinforcement to slidably disengage during use.

The reinforcement plate 178 is preferably made by injection molding from plastic such as HDPE. In contrast, the back plate 124 is made from a rigid material such as cardboard that deteriorates shortly after being saturated with a cleaning solution. Deterioration after a single use is intended so that a technician does not re-use the cleaning tool on different machines and spread contamination from one machine to another. The cardboard back plate 124 has a coating that ensures the back plate remains rigid during the initial, single use.

Referring to FIG. 12, the grain of the cardboard "G" is preferably oriented lengthwise from front to back. This preferred orientation helps the cartridge to deflect into a widthwise-arcuate shape approaching the contour of the scanner bore when the tool is inserted into either the front or back of the patient scanner. Arcuate deformation increases surface area contact between the cleaning pad 122 and the arcuate walls of the patient scanner.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

The invention claimed is:

1. A cleaning device, comprising:
   a) an elongate wand having a central body and first and second ends, b) a handle at the first end of said wand;
   c) a cleaning cartridge having a cleaning pad and a back plate with an attachment portion; and,
   d) means for releasably attaching and detaching the cleaning cartridge to the second end of the wand, having:
      i) an ejector collar slidably fixed to the second end of said wand and movable between extended and retracted positions, said collar including a pair of collar jaws;
      ii) a pair of clamp jaws on the second end of said wand lying within said ejector collar, said clamp jaws being in near abutment with an inside surface of said collar when said collar is in the retracted position;
   wherein said cartridge is attached to said wand by inserting the attachment portion of said back plate between said clamp jaws and clamping said clamp jaws on said attachment portion of said back plate; and
   wherein said cartridge is detached from said wand by pushing said ejector collar along said wand body away from said second end of said wand and against the cartridge.

2. The cleaning device of claim 1, said ejector collar including a nose portion along an outside surface of a distal end thereof and said cartridge including a rimmed pocket, wherein movement of said ejector collar from the retracted position towards its extended position moves said nose portion into forcible engagement with the rim of said pocket.

3. The cleaning device of claim 2, wherein said pocket abuts closely-fitting side surfaces of said ejector collar nose.

4. The cleaning device of claim 1, wherein the inside surface of said collar is convergent in the direction of said nose portion such that when said collar is in the extended position there is a substantial gap between the outside surface of said wand jaws and the inside surface of the collar permitting the clamp jaws to open.

5. The cleaning device of claim 1, wherein said back plate attachment portion includes a pivotal hinge that permits said cartridge to rotate with respect to the wand.

6. The cleaning device of claim 1, wherein said back plate attachment portion is received between and clamped by said clamp jaws, and said back plate attachment portion includes an upwardly-extending nub that is captured behind said clamp jaws, to resist movement of said cartridge when attached to said wand.

7. The cleaning device of claim 1, said wand body further including an elongate opening through a sidewall thereof, said opening cooperating with a stop projecting radially inwardly from said collar, wherein said stop engages an inside wall of the opening to limit the movement of said collar with respect to said wand.

8. The cleaning device of claim 1, wherein said central body is arcuate.

9. The cleaning device of claim 1, wherein said cleaning pad is an absorbent pad at least partially saturated with a liquid disinfectant.

10. The cleaning device recited in claim 1, wherein said ejection collar includes a pair of ejection jaws and said leaf includes a pocket into which the collar nests when the cartridge is connected to said wand.

11. The cleaning device recited in claim 10, wherein said ejection jaws and said clamp jaws are coaxial and have generally-coplanar clamping surfaces.

12. A cleaning device, comprising:
   a) a wand having an elongate central body with first and second opposed ends, and a handle on the first end;
   b) a disposable cleaning cartridge having a cleaning pad and a supporting back plate fixed to said pad;
   c) mechanism for releasably attaching said cleaning cartridge to the second end of said wand, said attachment mechanism including:
      i) a leaf hinged to said back plate; and,
      ii) a clamp connected to the second end of said wand, said clamp including a pair of clamp jaws that releasably engage opposed sides of said leaf; and,
   d) mechanism for detaching said cleaning cartridge from said wand without handling said cleaning cartridge, including an ejection collar slidably affixed to said second end of said wand and movable between extended and retracted positions, said ejection collar being constructed and arranged to allow said leaf to engage with said clamp when said collar is in the retracted position, and to eject said leaf from engagement with said clamp when said collar is moved from the retracted position to the extended position.

13. The cleaning device recited in claim 12, wherein said leaf comprises a tab partially cut from said back plate and partially connected to and rotatable relative to said plate along a linear hinge interface.

14. The cleaning device recited in claim 13, wherein said hinge interface comprises a linear, reduced-thickness section of said back plate.

15. The cleaning device recited in claim 12, wherein said collar envelopes said clamp and is movable relative thereto.

16. The cleaning device recited in claim 13, wherein said clamp includes a bore in said clamp jaws and said tab includes a detent that passes through said socket.

17. The cleaning device recited in claim 16, wherein said detent comprises a nub on the tab and the bore is arranged so that the nub is captured adjacent the clamping surface of said jaws to resist axially-disengaging movement from said clamp.

18. The cleaning device recited in claim 17, wherein said clamp jaws are elastically deformable and said nub has a hemispherical shape.

19. The cleaning device recited in claim 18, wherein said clamp jaws impose an axial force on said tab when the apex of said nub clears the clamping surface of said clamp jaws.

20. A cleaning device, comprising:
   a) a wand having an elongate central body with first and second opposed ends, and a handle on the first end;
   b) a container of a plurality of individual, pre-packaged, disposable cleaning cartridges having a cleaning pad, a supporting back plate fixed to said pad, and a cleaning solution impregnated in said cleaning pad;
   c) mechanism for releasably attaching said cleaning cartridge to the second end of said wand, said attachment mechanism including:
      i) a leaf hinged to said back plate; and,
      ii) a clamp connected to the second end of said wand, said clamp including a pair of clamp jaws that releasably engage opposed sides of said leaf; and,
   d) mechanism for detaching said cleaning cartridge from said wand without handling said cleaning cartridge, including an ejection collar slidably affixed to said second end of said wand and movable between extended and retracted positions, said ejection collar being constructed and arranged to allow said leaf to engage with said clamp when said collar is in the retracted position, and to eject said leaf from engagement with said clamp when said collar is moved from the retracted position to the extended position.

* * * * *